(12) United States Patent
Dellinger et al.

(10) Patent No.: US 6,743,585 B2
(45) Date of Patent: Jun. 1, 2004

(54) METHODS FOR PREPARING CONJUGATES (75) Inventors: Douglas J. Dellinger, Sunnyvale, CA (US); Joel Myerson, Berkeley, CA (US); Geraldine Fulcrand, Sunnyvale, CA (US); Diane D. Ilsley, San Jose, CA (US)

(73) Assignee: Agilent Technologies, Inc., Palo Alto, CA (US)

(*) Notice: Subject to any disclaimer, the term of this patent is extended or adjusted under 35 U.S.C. 154(b) by 41 days.

(21) Appl. No.: 09/981,580

(22) Filed: Oct. 17, 2001

(65) Prior Publication Data
US 2002/0025539 A1 Feb. 28, 2002

Related U.S. Application Data (62) Division of application No. 09/397,526, filed on Sep. 16, 1999, now abandoned.

(51) Int. Cl.[7] .................. C12Q 1/68; G01N 33/552; G01N 33/545; G01N 33/553; G01N 33/549
(52) U.S. Cl. ............... 435/6; 435/188; 436/525; 436/527; 436/529; 436/530; 436/531; 436/532; 436/829; 530/391.1; 530/402; 530/409
(58) Field of Search ............... 435/6, 188; 436/530, 436/531, 532, 529, 527, 525, 829; 530/391.1, 402, 409

(56) References Cited

U.S. PATENT DOCUMENTS

| | | | |
|---|---|---|---|
| 4,150,105 A | 4/1979 | Gross | |
| 4,436,823 A | 3/1984 | Blumcke et al. | 436/169 |
| 4,562,157 A | 12/1985 | Lowe et al. | 435/291 |
| 4,623,629 A | 11/1986 | Kerschensteiner | |
| 5,077,210 A | 12/1991 | Eigler et al. | 435/176 |
| 5,192,661 A | 3/1993 | Roy et al. | 435/7.23 |
| 5,232,859 A | 8/1993 | Kapmeyer et al. | 436/518 |

(List continued on next page.)

FOREIGN PATENT DOCUMENTS

| EP | 0 786 468 | 7/1997 |
|---|---|---|
| EP | 0 839 829 | 5/1998 |
| WO | WO 90/05749 | 5/1990 |

OTHER PUBLICATIONS

C. Bonnard et al, Chem. Abstract No. 1989: 52757 (1989).*
F. Kaspersen et al, Chem. Abstract No. 1976: 43950 (1976).*
A. Pohland et al, Chemical Reviews, vol. 66, pp. 161–197 (1966).*
Mandenius, Carl F. et al., "The Interaction of Proteins and Cells with Affinity Ligands Covalently Coupled to Silicon Surfaces as Monitored by Ellipsometry", Analytical Biochemistry, vol. 137, 1984, pp. 106–114.
Truce, et al., *J. Org. Chem.*, 35(7): 2113–2117, (1970); Stereochemistry of Nucleophilic Displacements by Amines on Activated Vinyl Halides.
Jones, et al., *J. Chem. Soc.*, 2349–2366, (1960); Substitution at an Olefinic Carbon. The Reactions of the Ethyl β–Chlorocrotonates with Nucleophiles.
Pohland, et al., *Chem. Rev.*, 66: 161–197, (1966); β–Chlorovinyl Ketones.

(List continued on next page.)

Primary Examiner—Mary E. Ceperley (57) ABSTRACT

Methods are disclosed for conjugating one moiety to another moiety. In the method the moieties are reacted with one another in a protic solvent. Reaction between the moieties and the protic solvent during the conjugating is negligible or reversible. A stable bond is formed between the moieties to produce a product that is not subject to β-elimination at elevated pH. Usually, one of the moieties comprises an unsaturation between two carbon atoms. One of the carbon atoms is or becomes an electrophile during the conjugating. The other of the moieties comprises a functionality reactive with the electrophile carbon atom to form a product that comprises the unsaturation. Compounds comprising both of the moieties as well as precursor molecules are also disclosed. Methods are also disclosed for determining an analyte in a sample employing compounds as described above.

7 Claims, 2 Drawing Sheets

U.S. PATENT DOCUMENTS

| | | | |
|---|---|---|---|
| 5,294,536 A | 3/1994 | Palumbo | 435/7.93 |
| 5,372,930 A | 12/1994 | Colton et al. | 435/6 |
| 5,389,523 A | 2/1995 | Plant et al. | 435/7.92 |
| 5,397,695 A | 3/1995 | Sutton et al. | 435/5 |
| 5,405,783 A | 4/1995 | Pirrung et al. | 436/518 |
| 5,459,078 A | 10/1995 | Kline et al. | 436/518 |
| 5,459,080 A | 10/1995 | Adamczyk et al. | 436/538 |
| 5,525,734 A | 6/1996 | Gallop et al. | 548/453 |
| 5,532,170 A | 7/1996 | Buckle et al. | 436/527 |
| 5,545,568 A | 8/1996 | Ellman | 436/518 |
| 5,624,711 A | 4/1997 | Sundberg et al. | 427/261 |
| 5,639,626 A | 6/1997 | Kiaei et al. | 435/7.92 |
| 5,656,506 A | 8/1997 | Kawaguchi et al. | 436/534 |
| 5,663,306 A | 9/1997 | Aldwin et al. | 530/402 |
| 5,665,868 A | 9/1997 | Ramadoss et al. | 530/412 |
| 5,677,432 A | 10/1997 | Jones et al. | 530/404 |
| 5,717,075 A | 2/1998 | Boyd et al. | 530/402 |
| 5,723,344 A | 3/1998 | Mabilat et al. | 436/518 |
| 5,744,101 A | 4/1998 | Fodor et al. | 422/131 |
| 5,750,357 A | 5/1998 | Olstein et al. | 435/7.32 |
| 5,766,963 A | 6/1998 | Baldwin et al. | |
| 5,783,627 A | 7/1998 | Kao et al. | 525/54.1 |

OTHER PUBLICATIONS

Scotti. et al., *J. Org. Chem., 29*: 1800–1808, (1964); The Synthesis and Reactions of β–Chloroacrylonitrile.

Landini, et al., *J. Chem. Soc. B,* 243–247, (1969); Nucleophilic Substitution and Elimination in 2–Halogenovinyl Ketones.

Farina, et al., *Synthesis, 9:* 642–644, (1977); Pseudoesters and Derivatives: VIII. Synthesis of 4,4–Dimethoxy–2–butynoic Acid Derivatives.

Yogo, et al., *J. Chem. Soc. Perkin Trans., 1*(9): 2097–2102, (1984); Synthesis of 5lminopyrrol–2–one Derivatives from 1,3–Oxazines. Ring Transformations via Attack on the 2– or 6–Position of 1,3–Oxazines.

Rao, et al., *Synthetic Communications, 19*(7&8): 1431–1436, (1989); A Mild and Efficient Procedure for Dehydration of Primary Carboxamides to Nitriles by Silyl Sulphonyl Polyphosphates.

Bryant, et al., *J. Heterocyclic Chem., 32*: 1473, (1995); A Large Scale Synthesis of 3–Chloro–5–methoxypyridazine.

Ichikawa, et al., *Synlett, 3*: 243–245, (1996); The Reaction of 2,2–Difluorovinyl Ketones with Amines: A Facile Methodfor Preparation of α–Oxoketenimines and Acetoacetylation of Amines.

Jalander, Lars F., *Acta Chem. Scand., 49*(12): 894–898, (1995); Nucleophilic Vinylic Substitutions of (E)– (Z)–Ethyl 3–Aryl–3chloro–2–cyanopropenoates with Thioureas. Synthesis of 1,3–Thiazin–4–ones.

Tominaga, et al., *Chem. Pharm. Bull., 32*(6): 2100–2101, (1984); Studies on Positive Inotropic Agents. I. Synthesis of 3,4–Dihydro–6–[4–(3, 4–dimethoxybenzoyl)–1–piperazinyl]–2(1H)–quinolinone and Related Compounds.

Nishigaki, et al., *Chem. Pharm. Bull., 28*(1): 142–149, (1980); Synthesis of 1,3–Dimethylpyrimido[4,5–b]quinoline–2,4(1H,3H)–diones(1,3–Dimethyl–5–deazalloxazines) and Related Compounds via the Intramolecular Cycloaddition of Azahexatrienes.

Winkler, et al., *Tetrahedron Letters, 30*(42): 5703–5704, (1989); Intramolecular Photocycloaddition and Retro–Mannich Fragmentation of Acyclic Teriary Vinylogous Amides.

* cited by examiner

METHODS FOR PREPARING CONJUGATES

CROSS REFERENCE TO RELATED APPLICATION(S)

This is a divisional of application Ser. No. 09/397,526 filed on Sep. 16, 1999, abandoned.

BACKGROUND OF THE INVENTION

1. Field of the Invention

This invention relates to the covalent attachment of one moiety to another moiety such as a ligand to a surface or to another ligand, a ligand to a receptor, a receptor to a surface, and the like. The invention also relates to reagents for conducting such covalent attachment and methods for using such reagents.

In the field of diagnostics and therapeutics it is often useful to attach species or to couple different species together so as to alter or improve their properties. For example, although haptens, short peptides and the like function poorly as immunogens, a vigorous immune response may be elicited by coupling these moieties to larger moieties such as a protein carrier. In general, haptens (antigens), biotin, drug derivatives or peptides may be covalently bonded to proteins or natural or synthetic polypeptides for use as immunogens or recognition tags, or to enzymes for use in homogeneous enzyme immunoassays or to other label moieties for use in specific binding assays.

Similarly, antibodies may be coupled to toxins for use as immunotoxins, or to enzymes for use in enzyme immunoassays. The attachment of cytotoxic drugs to tumor-localizing monoclonal antibodies is an approach to chemotherapy that is gaining acceptance. Many reagents for the preparation of such conjugates have been disclosed and studied extensively. The so-called cross-linking reagents that have been developed are typically designed to have specific reactivity with functional groups contained in each reactant. Both homo- and heterobifunctional reagents are known with the latter being most widely used.

Active agents that are preferably functional organic material such as proteins have been immobilized in the past on a wide variety of solid supports for various known applications including analysis, separation, synthesis and detection of biological and other materials. Often hydrophilic polymers have been used to immobilize proteins because it is less difficult to attach proteins to polymers than to inorganic materials. However, there is an increasing need to immobilize functional organic material such as proteins on inorganic material such as silica, glass, silicon, metals and the like. In solid phase technology the reagent or reagents used in the procedure are usually immobilized by being coated or bonded either covalently or by adsorption to the solid phase material.

Biologically active polypeptides or proteins that are attached to an insoluble carrier material, such as polymeric particles, have been used in a variety of ways. For example, the diagnosis of pathological or other conditions in human beings and animals is often carried out using immunological principles for the detection of an immunologically reactive species, for example, antibodies or an antigen, in the body fluids of the person or animal. Other proteins and amine-containing compounds, such as enzymes, avidin, biotin or polysaccharides, have been covalently linked to various carrier materials for use in affinity chromatography, enzymatic reactions, specific binding reactions and immunoassays.

In the field of bioscience, arrays of oligonucleotide probes, fabricated or deposited on a surface, are used to identify DNA sequences in cell matter. The arrays may be used for conducting cell study, for diagnosing disease, identifying gene expression, monitoring drug response, determination of viral load, identifying genetic polymorphisms, and the like. Significant morbidity and mortality are associated with infectious diseases and genetically inherited disorders. More rapid and accurate diagnostic methods are required for better monitoring and treatment of these conditions. Molecular methods using DNA probes, nucleic acid hybridization and in vitro amplification techniques are promising methods offering advantages to conventional methods used for patient diagnoses.

A variety of methods have been reported for the covalent attachment of ligands to a surface or for the attachment of small molecule tags on to biomolecules or for the attachment of biomolecules to each other. Typically, these reactions are performed by the reaction of an active functional group on one molecule with an activated functional group on another. As an example, an amine containing fluorophor can be attached to a carboxylic acid containing surface by forming an activated ester of the carboxylic acid, such as an N-hydroxysuccinimide derivative. The amine readily reacts with this activated ester to form a stable amide bond. This reaction is useful under conditions whereby the reaction with the desired amine is significantly faster than with other nucleophiles in the system.

Methods previously described include the activation of surfaces with cyanogen bromide, N-hydroxysuccinimide esters, carbonyl diimidazole, carbodiimides, azlactones, cyanuric chlorides, organic sulfonyl chlorides, divinyl sulphone, nitrophenyl esters, iodoacetyl, maleimide, epoxy, hydrazide, reductive amination, diazonium salts and Mannich condensations. Ligands that react with the activated surface include amines, alcohols, carboxylic acids, thiols, carbonyls, and compounds containing active hydrogens.

The attachment of two generally polyfunctional molecules at defined reaction loci presents a considerable challenge. The bond that is formed must be stable under the desired conditions of use. Another factor is that the system must not produce side reactions that will destroy the ability of the ligand to react with an activated functionality. When the reaction is performed in aqueous or protic solvent systems, the desired reaction can compete with solvent molecules for product formation. The resulting side products thus significantly lower the yield of the desired reaction. Nearly all of the commonly used methods of surface attachment and bioconjugation are susceptible to these solvolysis problems. For example, in an aqueous solvent system, when coupling an amine to a surface activated with an N-hydroxysuccinimide ester, the hydrolysis reaction of the activated ester can complete with the desired amine coupling. The activated functionality can react with the solvent, usually water, instead of with the desired ligand. In order for the coupling reaction to be successful, the reaction rate of the ligand with the activated functionality must be fast relative to the deactivation of the functional group, or a large enough excess of activated functional group must be present.

2. Description of the Related Art

U.S. Pat. No. 4,623,629 (Kerachensteiner) discloses a solid phase immunoassay support and method of use thereof.

U.S. Pat. No. 5,766,963 (Baldwin, et al.) discusses a combination hydroxypropylamine library.

Conjugated polypeptides and methods for their preparation and use are discussed in PCT application WO 90/05749 (Schultz).

Stereochemistry of nucleophilic displacements by amines on activated vinyl halides is discussed by Truce, et al., *J. Org. Chem.* (1970) 35(7):2113–2117.

Jones, et al., describe the substitution at an olefinic carbon, the reactions of the ethyl β-chlorocrotonates with nucleophiles (*J. Chem. Soc.* (1960) 2349–2366).

β-Chlorovinyl ketones are discussed by Pohland, et al., in *Chem. Rev.* (1966) 66:161–197.

The synthesis and reactions of β-chloroacrylonitrile are disclosed by Scotti, et al., *J. Org. Chem.* (1964) 29:1800–1808.

Landini, et al., *J. Chem. Soc. B* (1969) 243–247, describe the nucleophilic substitution and elimination in 2-halogenovinyl ketones.

Farina, et al., *Synthesis* (1977) 642, describes the synthesis of a β-bromovinyl ester.

Yogo et al. *J. Chem. Soc.*, (1984), 2097, describes the synthesis of a β-bromovinyl imide.

Rao, et al., *Synth. Comm.* (1989), 19 describe the synthesis of a β-chlorovinyl amide.

Bryant, et al., *J. Heterocyclic Chem.* (1995), 32: 1473–1476 describes the reaction of an alcohol with a β-chlorovinyl amide.

Ichikawa, et al. Synlett (1966), 243, describe the reaction of a primary amine with a β-fluorovinyl ketone.

Jalander, *Acta Chem. Scand.* (1995), 49: 894–898, describe the reaction of a thiourea with a β-chlorovinyl ester.

Tominaga, et al., *Chem. Pharm. Bull* (1984), 32: 2100, describe the reaction of a secondary amine with a β-chlorovinyl amide.

Nishigaki, et al., *Chem. Pharm. Bull*, (1980), 28: 142 describe the reaction of an aromatic amine with a disubstituted β-chlorovinyl amide derivative.

Winkler et al., *Tetrahedron Lett.* (1989) 30, describe the reaction of an amine with a β-chlorovinyl ketone.

SUMMARY OF THE INVENTION

One aspect of the present invention is a method for conjugating one moiety to another moiety. In the method molecules comprising the moieties are reacted with one another in a protic solvent. Reaction between the moieties and the protic solvent during the conjugating is negligible or reversible. A stable bond is formed between the moieties to produce a product that is not subject to β-elimination at elevated pH.

Another aspect of the present invention is a method for conjugating one moiety to another moiety. A combination comprising the moieties is formed in a reaction medium. One of the moieties comprises an unsaturation between two carbon atoms. One of the carbon atoms is or becomes an electrophile during the conjugating. The other of the moieties comprises a functionality reactive with the electrophile carbon atom to form a product that comprises the unsaturation. The medium is subjected to conditions under which the product is formed.

Another aspect of the present invention is a method for conjugating one moiety to another moiety. A combination is provided in a medium. The combination comprises a first reagent, M1-L1-Z, wherein M1 is a first moiety, L1 is a bond or a linking group and Z is a nucleophile, and a second reagent, X—C(L2R)=C(L3R$^1$)—Y(L4R$^2$), wherein one of R, R$^1$ or R$^2$ is a second moiety and L2, L3 and L4 are independently a bond or a linking group. X is a leaving group or X and R$^1$ may be taken together to form a bond. Y is a substituent that renders the carbon bearing the L2R group an electrophile. When not a second moiety, R, R$^1$ and R$^2$ may be independently any group, aliphatic or aromatic, which does not interfere with the desired reaction to any significant extent. When R and R$^1$ or R and R$^2$ are not a second moiety, R and R$^1$ or R and R$^2$ may be taken together to form a 5 to 7 membered ring. When R or R$^1$ are not a second moiety, Y may be taken together with R or R$^1$ to form a 5 to 7 membered ring. The combination is incubated under conditions sufficient to permit the formation of a product of the reaction of the first and second reagents wherein M1 becomes conjugated to the second reagent.

Another aspect of the present invention is a method for conjugating one moiety to another moiety. The moieties are independently selected from the group consisting of ligands and surfaces. A combination is provided comprising a first reagent, M1'-L1'-Z', wherein M1' is a first moiety, L1' is a bond or a linking group and Z' is an amine group and a second reagent, X'—CH=CH—(C=O)(L4'M2'), wherein M2' is a second moiety and L4' is a bond or a linking group. X' is selected from the group consisting of fluoro, bromo, chloro and iodo. The combination is treated under conditions sufficient to permit the formation of a product of the reaction of the first and second reagents wherein Z' displaces X' in the second reagent. M1' becomes conjugated to the second reagent to form a product of the formula: M1'L1'—NH—CH=CH—(C=O)(L4'M2').

Another aspect of the present invention is a conjugate of the formula:

M1-Z—C(L2'R$^3$)=C(L3'R$^4$)—Y—(L4"R$^5$)

wherein M1 is a first moiety and Z is a heteroatom, and
wherein L2', L3' and L4" are independently a bond or a linking group; and
wherein one of R$^3$, R$^4$ or R$^5$ is a second moiety; and
wherein Y is a substituent that comprises a carbon-carbon double bond, a carbon-heteroatom double bond or a carbon-nitrogen triple bond wherein, when Y is a carbon-carbon double bond or a carbon-heteroatom double bond, Y may be taken together with R$^3$ or R$^4$ to form a 5 to 7 membered ring when R$^3$ or R$^4$ are not a second moiety; and
wherein, when not a second moiety, R$^3$, R$^4$ and R$^5$ are independently selected from the group consisting of H, alkyl, alkenyl, alkynyl, aryl, aralkyl, heteroalkyl, heteroalkenyl, heteroalkynyl, heteroaryl, heteroaralkyl, and the like; and
wherein, when R$^3$ and R$^4$ or R$^3$ and R$^5$ are not a second moiety, R$^3$ and R$^4$ or R$^3$ and R$^5$ may be taken together to form a 5 to 7 membered ring.

Another aspect of the present invention is a compound of the formula:

M1-NH—CH=CH—(C=O)(L4'M2)

wherein M1 is a first moiety and M2 is a second moiety and L4' is a bond or a linking group.

Another aspect of the present invention is a compound of the formula:

X'—CH=CH—(C=O)(L4'M2")

wherein M2" is a moiety, L4' is a bond or a linking group and X' is selected from the group consisting of fluoro, bromo, chloro and iodo.

Another aspect of the present invention is a method for determining an analyte in a sample. A combination is provided comprising in a medium the sample and at least one compound mentioned above. The compound forms a complex related to the presence of the analyte in the sample. The presence of the compound in the complex is detected, the presence thereof indicating the presence of the analyte.

DEFINITIONS

Before proceeding further with a description of the specific embodiments of the present invention, a number of terms will be defined.

Conjugating—the process whereby one moiety becomes attached, usually covalently attached, to another moiety.

Moiety—a species to be joined to another species. In general, the moiety may be a ligand, receptor or a surface.

Ligand—the ligand may be an organic compound, which may be either a small molecule or a large or macromolecule, or it may be an inorganic material such as a metal particle or the like. The ligand may be a protein, peptide, polysaccharide, hormone, nucleic acid, liposome, cell, label including a particle, hapten, drug, inhibitor, dye, and so forth.

For the most part, the large molecule ligands to which the subject invention can be applied include poly(amino acids), e.g., proteins, large peptides, polysaccharides, hormones, nucleic acids, soluble polymers, metal colloids and so forth. The large molecules generally have a molecular weight of at least about 5,000, more usually at least about 10,000. In the poly(amino acid), polysaccharide or nucleic acid category, the molecules are generally from about 5,000 to 5,000,000 molecular weight, more usually from about 20,000 to 1,000,000 molecular weight. In the hormone category, the molecular weights usually range from about 5,000 to 60,000.

A wide variety of proteins are included within the term "large molecules." Such proteins include proteins having particular biological functions, proteins related to specific microorganisms, particularly disease causing microorganisms, etc. Exemplary of such proteins are immunoglobulins, cytokines, enzymes, hormones, cancer antigens, nutritional markers, tissue specific antigens, etc. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, a-fetoprotein, acid phosphatase, CA19.9 and CA125, tissue specific antigens, such as, e.g., alkaline phosphatase, myoglobin, CPK-MB and calcitonin, and peptide hormones.

Polynucleotides include DNA, RNA, m-RNA, r-RNA, t-RNA, cDNA, DNA-RNA duplexes, etc.

The small molecules are generally of molecular weight less than about 5,000, more usually less than about 2000 and include haptens, which are molecules that are not immunogenic by themselves but can be rendered immunogenic by being attached to a large molecule. Usually, the lower molecular weight or small molecules are generally of from about 100 to 2,000 molecular weight, more usually from 125 to 1,000 molecular weight. The small molecules include drugs, metabolites, pesticides, pollutants, dyes, lower molecular weight peptides, oligonucleotides, modified nucleotides, modified oligonucleotides and so forth.

The term "drug" includes alkaloids, steroids, barbituates, amphetamines; catecholamines, benzheterocyclics, the heterocyclic rings being azepines, diazepines and phenothiazines, purines, which includes theophylline, caffeine, drugs derived from marijuana, hormones vitamins, prostaglandins, tricyclic antidepressants, anti-neoplastics, antibiotics, nucleosides and nucleotides, opiods, miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives, aminoglycosides and the like.

Metabolites related to diseased states include spermine, galactose, phenylpyruvic acid, and porphyrin Type 1. Among pesticides are polyhalogenated biphenyls, phosphate esters, thiophosphates, carbamates, polyhalogenated sulfenamides, their metabolites and derivatives.

Receptor—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq, and the like. The term "receptor" also includes polynucleotide binding agents, such as, for example, restriction enzymes, activators, repressors, nucleases, polymerases, histones, repair enzymes, chemotherapeutic agents, and the like. For receptors, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc. As can be seen there is some overlap between large molecular ligands on the one hand and receptors on the other hand.

Protic solvent—a solvent capable of losing or gaining a proton from a molecule that is contained therein.

Reversible—pertains to a chemical reaction that can proceed in either direction, i.e., direction of starting materials or direction of products, and is usually incomplete, thus, establishing an equilibrium.

Stable bond—a bond that is not readily destroyed or uncoupled.

β-Elimination—elimination of a substituent from a β-carbon atom.

Enamine functionality—a functionality represented by the formula >C=C—N<.

Unsaturation—a condition usually represented by the presence of at least one double bond, triple bond or ring in a molecule.

Leaving group—a group that is subject to displacement by another group. In general, there is a reasonable correlation between the ability of a group to be displaced and the acid strength of the group when bound to hydrogen. The stronger the acid that comprises the group, the better the leaving capability of the leaving group.

Linking group—the linking group may be a chain of from 1 to 100 atoms, usually from about 1 to 70 atoms, preferably, 1 to 50 atoms, more preferably 1 to 20 atoms, each independently selected from the group normally consisting of carbon, oxygen, sulfur, nitrogen, halogen and phosphorous. The number of heteroatoms in the linking groups will normally range from about 0 to 20, usually from about 1 to 15, more preferably 2 to 6. The atoms in the chain may be substituted with atoms other than hydrogen, which may be a single atom such as a halogen, etc., or part of a group of atoms forming a functionality such as oxo or oxy, nitro, nitroso or amino, normally bonded to carbon, phosphonate and phosphate mono- or diester. The linking groups may be aliphatic or aromatic.

For the most part, a linking group prior to linking will have a functionality for linking such as a non-oxocarbonyl group including nitrogen and sulfur analogs, a phosphate group, an amino group, alkylating agents such as halo or tosylalkyl, oxy (hydroxyl or the sulfur analog, mercapto) oxocarbonyl (e.g., aldehyde or ketone), or active olefin such as a vinyl sulfone or α-, β-unsaturated ester. These functionalities will be linked to amine groups, carboxyl groups, nucleophiles (e.g. hydroxyl, thiol). Where an amine and carboxylic acid or its nitrogen derivative or phosphoric acid are linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed.

The composition and length of the linking group is not critical to the present invention. It is often preferred that the linking group be hydrophilic or aqueous friendly. As a general rule, the length of a particular linking group can be selected arbitrarily to provide for convenience of synthesis and the incorporation of any desired moiety. The linking group should not contain functionalities, or be of a length, that will interfere with the reactions that are desired in accordance with the present invention. Furthermore, the chemistry used to introduce the linking group should not be detrimental to the molecule in question. The linking group may be the result of reacting certain reactive functionalities as mentioned above. The binding provided by the linking group should be sufficiently stable to achieve the benefits in accordance with the present invention.

In certain situations it may be desirable to provide labile linking groups which are degraded under preselected conditions. For example, the linking group may be chemically or biologically labile where a polynucleotide is constructed on the surface and it is desirable to release the polynucleotide from the surface. Other examples of the use of a labile linking group in the present invention will be apparent to those skilled in the art.

Examples of particular linking groups that may be used in accordance with the present invention include by way of illustration and not limitation, alkylene oxide chain comprising repeating units of alkylene and oxygen in an ether linkage, alkylene imine chain comprising repeating units of alkylene and nitrogen as an imine linkage and the like. For example, the alkylene oxide may be represented by the formula: $-[(CH_2)_m-O-(CH_2)_n-O-(CH_2)_p-O-(CH_2)_s]_q-$ wherein m, n, p and s are each independently an integer of 2 to 4 and q is an integer of 1 to 5, preferably 1 to 3, more preferably 1. For example, the alkylene imine may be represent by the formula: $-[(CH_2)_m-NR-(CH_2)_n-NR-(CH_2)_p-NR-(CH_2)_s]_q-$ herein R is H or alkyl, m, n, p and s are each independently an integer of 2 to 4 and q is an integer of 1 to 5, preferably 1 to 3, more preferably 1. The alkylene moiety in the above may be optionally substituted with one or more groups such as alkyl, alkylene, aryl, alkaryl, hetero derivatives thereof, and the like.

Electrophile—the state of being electron poor. A carbon atom is an electrophile, or electrophilic, when it is electron deprived or has an overall positive charge relative to another portion of a molecule, i.e., has reduced electron density. This may result from the presence of a substituent that renders the carbon in question an electrophile, namely, a substituent that promotes the resonance of electrons away from the carbon atom in question.

Functionality reactive with an electrophile—a functionality that is reactive with a carbon that is an electrophile by virtue of being of opposite electron density than that of such carbon. Usually, such a functionality is a nucleophile, i.e., it is electron rich and able to donate its electrons, usually an electron pair, to an electrophile. The nucleophilicity of a molecule does not coincide with its basicity or its ability to donate an electron pair to a proton. Generally, strong bases are good nucleophiles but weak bases may also be good nucleophiles.

Surface—the outer portion of a support, which is a porous or non-porous water insoluble material. The support can have any one of a number of shapes, such as strip, plate, disk, rod, particle, including bead, tube, well, and the like. The support can be hydrophilic or capable of being rendered hydrophilic and can be porous or non-porous, and includes inorganic powders or particles such as glass, silica, silica gel, controlled pore glass, magnesium sulfate, and alumina; fused silica, quartz; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; composites, thin films: glass, borosilicate glass, glass available as Bioglass®, ceramics, metals, and the like. Natural or synthetic assemblies such as liposomes, phospholipid vesicles, and cells are also included within the meaning of the term "support."

Label—any moiety that may be incorporated into a molecule for the purpose of detection. The label is often a member of a signal producing system. The label is capable of being detected directly or indirectly. In general, any reporter molecule that is detectable can be a label. Labels include (i) reporter molecules that can be detected directly by virtue of generating a signal, (ii) specific binding pair members that may be detected indirectly by subsequent binding to a cognate that contains a reporter molecule, (iii) mass tags detectable by mass spectrometry, (iv) oligonucleotide primers that can provide a template for amplification or ligation and (v) a specific polynucleotide sequence or recognition sequence that can act as a ligand such as for a repressor protein, wherein in the latter two instances the oligonucleotide primer or repressor protein will have, or be capable of having, a reporter molecule and so forth.

The reporter molecule can be isotopic or nonisotopic, usually non-isotopic, and can be a catalyst, such as an enzyme, a polynucleotide coding for a catalyst, promoter, dye, fluorescent molecule, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, a mass tag that alters the weight of the molecule to which it is conjugated for the mass spectrometry purposes, and the like. The reporter molecule can be a fluorescent group such as fluorescein, a chemiluminescent group such as luminol, a terbium chelator such as N-(hydroxyethyl) ethylenediaminetriacetic acid that is capable of detection by delayed fluorescence, and the like. The label can be a mass tag, cleavable or non-cleavable, capable of detection in mass spectrometry by virtue of its mass or a change in mass of a member of a signal producing system.

The label is often a part of a signal producing system, which includes all of the reagents required to produce a measurable signal. Components of the signal producing system other than the label may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like.

"Alkyl" means a branched or unbranched saturated monovalent hydrocarbon radical containing 1 to 30 or more carbon atoms, such as methyl, ethyl, propyl, tert-butyl, n-hexyl, n-octyl and the like. Alkyl includes lower alkyl.

"Lower alkyl" means a branched or unbranched saturated monovalent hydrocarbon radical containing 1 to 10 carbon atoms, such as methyl, ethyl, propyl, isopropyl, tert-butyl, butyl, n-pentyl and the like.

"Cycloalkyl" means a saturated monovalent monocyclic hydrocarbon radical containing 3–8 carbon atoms, such as cyclopropyl, cyclobutyl, cyclopentyl, cyclohexyl, cycloheptyl, cyclooctyl and the like.

"Alkylene" means a branched or unbranched saturated divalent hydrocarbon radical containing 1 to 30 or more carbon atoms, such as methylene, ethylene, propylene, 2-methylpropylene, 1,2-dimethylpropylene, pentylene, and the like. Alkylene includes lower alkylene.

"Lower alkylene" means a branched or unbranched saturated divalent hydrocarbon radical containing 1 to 6 carbon atoms, such as methylene, ethylene, propylene, 2-methylpropylene, 1,2-dimethylpropylene, pentylene, and the like.

"Alkenyl" means a branched or unbranched unsaturated hydrocarbon radical containing at least one ethenylic bond and 2 to 30 or more carbon atoms, such as ethenyl, propenyl, n-butenyl, isopropenyl, isobutenyl, n-pentenyl, isopentenyl and the like, unless otherwise indicated.

"Lower alkenyl" means a branched or unbranched unsaturated hydrocarbon radical containing at least one ethenylic bond and 2 to 6 carbon atoms, such as ethenyl, propenyl, n-butenyl, isopropenyl, isobutenyl, n-pentenyl, isopentenyl and the like, unless otherwise indicated.

"Lower alkenylene" means a branched or unbranched unsaturated divalent hydrocarbon radical containing at least one ethenylic bond and 2 to 6 carbon atoms, such as ethenylene, propenylene, 2-methylpropenylene, 1,2-dimethylpropenylene, pentenylene, and the like.

"Alkynyl" means a branched or unbranched unsaturated hydrocarbon radical containing at least one carbon-carbon triple bond and 1 to 30 or more carbon atoms, such as ethynyl, propynyl, 1-butynyl, 2-butynyl, 1-pentynyl, 2-pentynyl and the like, unless otherwise indicated.

"Aryl" means an organic radical derived from an aromatic hydrocarbon by the removal of one atom and containing one or more aromatic rings, usually one to four aromatic rings, such as, e.g., phenyl (from benzene), naphthyl (from naphthalene), etc.

"Aralkyl" means an organic radical comprising both alkyl and aryl moieties.

"Hetero" preceding any of the above terms (for example, heteroalkyl, heteroalkenyl, heteroalkynyl, heteroaryl, heteroaralkyl, and the like) means a group as defined above that comprises one or more heteroatoms. The group may comprise 1 to 20 or more heteroatoms. The groups may comprise a chain of atoms where the chain comprises carbon atoms and heteroatoms. Functionalities formed by the presence of heteroatoms within the chain of atoms include, for example, ethers, secondary amines, esters, and the like. The heteroatom may be at the point of attachment of the radical to the molecule to which the radical is attached. An example of such, by way of illustration and not limitation is the heteroalkyl radical "alkoxy," e.g., methoxy, ethoxy and so forth. The atoms in the chain may be substituted with atoms other than hydrogen, which may be a single atom such as a halogen, etc., or part of a group of atoms forming a functionality such as oxo or oxy, ethers, esters, nitro, nitroso or amino, amido, azo, normally bonded to carbon, phosphonate and phosphate mono- or diester, sulfonate, thioesters, thioamides and the like.

Heteroatom—any atom other than carbon, preferably, for example, oxygen, sulfur, nitrogen, halogen and phosphorous, Substituted—means that a hydrogen atom of a molecule has been replaced by another atom, which may be a single atom such as a halogen, etc., or part of a group of atoms forming, for example, a linking group or a functionality.

Member of a specific binding pair ("sbp member")—one of two different molecules, having an area on the surface or in a cavity which specifically binds to and is thereby defined as complementary with a particular spatial and polar organization of the other molecule. The members of the specific binding pair include ligand and receptor (antiligand). These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member.

Antibody—an immunoglobulin that specifically binds to and is thereby defined as complementary with a particular spatial and polar organization of another molecule. The antibody can be found in the blood of an animal or may be synthesized. Monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Polynucleotide—a compound or composition that is a polymeric nucleotide or nucleic acid polymer. The polynucleotide may be a natural compound or a synthetic compound. In the context of an assay, the polynucleotide is often referred to as a polynucleotide analyte. The polynucleotide can have from about 2 to 5,000,000 or more nucleotides. The larger polynucleotides are generally found in the natural state. In an isolated state the polynucleotide can have about 2 to 50,000 or more nucleotides, usually about 10 to 20,000 nucleotides, more frequently 100 to 10,000 nucleotides. It is thus obvious that isolation of a polynucleotide from the natural state often results in fragmentation. The polynucleotides include nucleic acids, and fragments thereof, from any source in purified or unpurified form including DNA (dsDNA and ssDNA) and RNA, including tRNA, mRNA, rRNA, mitochondrial DNA and RNA, chloroplast DNA and RNA, DNA/RNA hybrids, or mixtures thereof, genes, chromosomes, plasmids, the genomes of biological material such as microorganisms, e.g., bacteria, yeasts, viruses, viroids, molds, fungi, plants, animals, humans, and the like. The polynucleotide can be only a minor fraction of a complex mixture such as a biological sample. Also included are genes, such as hemoglobin gene for sickle-cell anemia, cystic fibrosis gene, oncogenes, cDNA, and the like.

Oligonucleotide—a polynucleotide, usually single stranded, usually a synthetic polynucleotide but may be a naturally occurring polynucleotide. The oligonucleotide(s) are usually comprised of a sequence of at least 2 nucleotides, preferably, 10 to 100 nucleotides, more preferably, 20 to 50 nucleotides, and usually 10 to 30 nucleotides, more preferably, 15 to 30 nucleotides. Methods of oligonucleotide synthesis include phosphotriester and phosphodiester methods (Narang, et al. (1979) Meth. Enzymol 68:90) and synthesis on a support (Beaucage, et al. (1981) Tetrahedron Letters 22:1859–1862) as well as phosphoramidite techniques (Caruthers, M. H., et al., "Methods in Enzymology," Vol. 154, pp. 287–314 (1988)) and others described in "Synthesis and Applications of DNA and RNA," S. A. Narang, editor, Academic Press, New York, 1987, and the references contained therein.

Oligonucleotide probe—an oligonucleotide employed to bind to a portion of a polynucleotide such as another oligonucleotide or a target nucleotide sequence. The design and preparation of the oligonucleotide probes are generally dependent upon the sensitivity and specificity required, the sequence of the target polynucleotide and, in certain cases, the biological significance of certain portions of the target polynucleotide sequence.

Nucleoside triphosphates—nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine (A), guanine (G), inosine (I), and derivatives and analogs thereof. The pyrimidine bases include cytosine (C), thymine (T), uracil (U), and derivatives and analogs thereof. Nucleoside triphosphates include deoxyribonucleoside triphosphates such as the four common deoxyribonucleoside triphosphates dATP, dCTP, dGTP and dTTP and ribonucleoside triphosphates such as the four common triphosphates rATP, rCTP, rGTP and rUTP.

The term "nucleoside triphosphates" also includes derivatives and analogs thereof, which are exemplified by those derivatives that are recognized and polymerized in a similar manner to the underivatized nucleoside triphosphates.

Nucleotide—a base-sugar-phosphate combination that is the monomeric unit of nucleic acid polymers, i.e., DNA and RNA. The term "nucleotide" as used herein includes modified nucleotides as defined below.

DNA—deoxyribonucleic acid.

RNA—ribonucleic acid.

Modified nucleotide—a unit in a nucleic acid polymer that contains a modified base, sugar or phosphate group. The modified nucleotide can be produced by a chemical modification of the nucleotide either as part of the nucleic acid polymer or prior to the incorporation of the modified nucleotide into the nucleic acid polymer. For example, the methods mentioned above for the synthesis of an oligonucleotide may be employed. In another approach a modified nucleotide can be produced by incorporating a modified nucleoside triphosphate into the polymer chain during an amplification reaction. Examples of modified nucleotides, by way of illustration and not limitation, include dideoxynucleotides, derivatives or analogs that are biotinylated, amine modified, alkylated, fluorophor-labeled, and the like and also include phosphorothioate, ring atom modified derivatives, and so forth.

Nucleoside—is a base-sugar combination or a nucleotide lacking a phosphate moiety.

Analyte—a molecule of interest, which may be a molecule found directly in a sample such as biological tissue, including body fluids, from a host, waste effluents and so forth. The term "analyte" includes ligands and receptors as defined above. Particular examples of analytes include antibodies, antigens, haptens, oligonucleotides including oligonucleotide probes and modified oligonucleotides, polynucleotides including modified polynucleotides, proteins, peptides, pollutants, pesticides, and the like. The sample can be examined directly or may be pretreated to render the analyte more readily detectable. The biological tissue includes excised tissue from an organ or other body part of a host and body fluids, for example, urine, blood, plasma, serum, saliva, semen, stool, sputum, cerebral spinal fluid, tears, mucus, and the like.

Electron-withdrawing group—a substituent which, when bound to a molecule, is capable of polarizing the molecule such that the electron-withdrawing group becomes electron rich and negatively charged relative to another portion of the molecule, i.e., has enhanced electron density.

Ancillary Materials—various ancillary materials will frequently be employed in methods for determining an analyte using compounds in accordance with the present invention. For example, buffers will normally be present in an assay medium, as well as stabilizers for the assay medium and the assay components. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like.

DETAILED DESCRIPTION OF THE INVENTION

In its broadest application the present invention is directed to a system for attaching moieties to one another in which reaction with protic solvent is negligible or reversible and which results in the formation of a stable bond. This is accomplished through the use of conjugate addition reactions that are insensitive to the present of water under the desired conditions. In addition, the final product is not subject to β-elimination at elevated pH. The unsaturation is present between two carbon atoms, one of which is or becomes an electrophile during the reaction. One of the moieties to be attached is present in the molecule bearing the unsaturation. The other of the moieties is present in a molecule that reacts with the electrophile by virtue of the presence of a nucleophile.

The reaction between the molecules containing the moieties and a protic solvent is negligible or reversible. The reaction is negligible in that such reaction does not occur to any detectable level or occurs to a level of less than 10%, preferably, less than 5%, more preferably, less than 1%. Such reaction is reversible where reaction occurs between one of the molecules and water but reverses to reform the molecule, which can then react to form a product in accordance with the present invention. This is in contrast with the reaction of, for example, an N-hydroxysuccinimide ester with water, which is not reversible to any appreciable extent and, thus, results in a lower yield of desired product. The present invention is distinguished from known methods involving nucleophilic addition to a double bond, which are reversible.

The present invention may be applied as a coupling alternative in any system for the coupling of moieties to one another whether the moieties are small molecules, large molecules, surfaces and the like. Accordingly, the present invention may be used as an alternative to, for example, avidin-biotin and digoxigenin-antidigoxigenin, which are two of the most utilized systems for coupling moieties, as well as to phenylboronic acid complexing. The biotin-avidin system utilizes the binding specificity of the protein avidin or streptavidin toward the cofactor biotin. The avidin-biotin system has been used in numerous applications. See Wilchek, et al., Methods in Enzymology (1990) vol. 184. The biotin-avidin system does possess limitations such as nonspecific binding generally attributed to the basicity of the avidin molecule, nonspecific binding attributed to the presence of carbohydrate residues on the avidin molecule, and background interference associated with the presence of endogenous biotin, which is ubiquitous in both eukaryotic and prokaryotic cells. The digoxigenin-antidigoxigenin system involves the use of the steroid hapten digoxigenin, an alkaloid occurring exclusively in digitalis plants and antibodies against digoxigenin. See Kessler, et al., Biol. Chem. Hoppe-Seyler (1990) 371:917–965. Although the system overcomes some of the disadvantages of the avidin-biotin system, it has the disadvantages including being an immunological system wherein attachment is non-covalent. As discussed in U.S. Pat. No. 5,648,470 (Stolowitz), many important biological molecules including carbohydrates, catecholamines, prostaglandins, ribonucleotides and steroids contain requisite functionalities for interacting with phenylboronic acid to form complexes. However, this technology suffers from the disadvantages of yielding non-covalent attachment and having a higher $K_D$ than the avidin-biotin system.

The benefits of the present invention may be achieved by providing a combination of reagents in a medium. The medium may be a protic solvent or an aprotic solvent. Usually, it is desirable to conduct reactions in a protic solvent because of the nature of the ligands, receptors and surfaces involved. The medium may be an aqueous medium that is solely water or that contains from about 0.01 to about 80 or more volume percent of a cosolvent such as an organic solvent. Such organic solvents include by way of illustration and not limitation oxygenated organic solvents of from 1–6, more usually from 1–4, carbon atoms, including alcohols such as methanol, ethanol, propanol, etc., ethers such as tetrahydrofuran, ethyl ether, propyl ether, etc., dimethylformamide, dimethylsulfoxide, 1,4-dioxane, N-methyl-2-pyrrolidone (NMP), acetonitrile and the like. Usually these cosolvents, if used, are present in less than about 70 weight percent, more usually in less than about 30 weight percent.

The pH for the medium will usually be in the range of about 4 to about 14, more usually in the range of about 6 to about 13, and preferably in the range of about 7 to about 12. The pH is generally selected to achieve optimum reaction between the molecules containing the moieties. Among the factors that must be considered are the pH dependence of the reactive molecules, the stability of the molecules at different pH values, and so forth. Various buffers may be used to achieve the desired pH and maintain the pH during the reaction. Illustrative buffers include acetate, borate, phosphate, carbonate, and the like. The particular buffer employed is not critical to this invention as long as the buffer does not react unintentionally with the moiety or other reagents. Further, in an individual reaction one or another buffer may be preferred.

The combination provided in the method of the present invention comprises a first reagent, M1-L1-Z, wherein M1 is a first moiety, L1 is a bond or a linking group and Z is a nucleophile, and a second reagent, X—C(L2R)=C(L3R$^1$)—Y(L4R$^2$), wherein one of the R, R$^1$ or R$^2$ is a second moiety and L2, L3 and L4 are independently a bond or a linking group.

Y is a substituent that renders the carbon bearing the L2R group an electrophile. In general, the Y substituent is an electron-withdrawing group. The Y substituent may be one that facilitates resonance of electrons involving the unsaturation ("first unsaturation") between the carbon atoms in the above formula so that the carbon bearing the L2R group is rendered an electrophile. To achieve this, the Y substituent may comprise a second unsaturation, which permits electrons from the first unsaturation to resonate in a resonance system created by the first and second unsaturations. Examples of the Y substituent by way of illustration and not limitation include C=O, C=S, C=NR$^7$ wherein R$^7$ is H or alkyl, C=N, C=C, nitrile, sulfoxide, sulfone, and the like.

X is a leaving group or X and R$^1$ may be taken together to form a bond. In the latter instance, a triple bond is present between the two carbon atoms in question.

When not a second moiety, R, R$^1$ and R$^2$ may be independently any group, aliphatic or aromatic, which does not interfere with the desired reaction to any significant extent. Thus, for example, R, R$^1$ and R$^2$ may be independently selected from the group consisting of H, alkyl, alkenyl, alkynyl, aryl, aralkyl, heteroalkyl, heteroalkenyl, heteroalkynyl, heteroaryl, heteroaralkyl, and the like. In one embodiment, R, $R^1$ and $R^2$ may be independently selected from the group consisting of H, alkyl, alkenyl, alkynyl, aryl, and aralkyl and the like. As explained in more detail hereinbelow, R, $R^1$ and $R^2$ may be attached to the molecule through a linking group.

When R and $R^1$ or R and $R^2$ are not a second moiety, R and $R^1$ or R and $R^2$ may be taken together to form a 5 to 7 membered ring. When R or $R^1$ are not a second moiety, Y may be taken together with R or $R^1$ to form a 5 to 7 membered ring. The ring may be, for example, a 5 to 7 membered cycloalkyl ring, which may contain one or more unsaturations such as for example, cyclopentyl, cyclohexyl, cycloheptyl, and corresponding ring systems with one or more unsaturations, usually, 1 to 2 unsaturations, more usually, one unsaturation. The 5 to 7 membered ring may be fused to one or more additional rings to yield a polycyclic system. The following are examples, by way of illustration and not limitation, of particular ring systems that may be present in the second reagent where the terms have the same meaning as mentioned above:

Y and $R^1$ taken together:

Y and R taken together:

wherein A is a substituent and X is a leaving group
R and $R^1$ taken together:

R and $R^2$ taken together:

X and $R^1$ taken together:

As explained above, when one of R, $R^1$ and $R^2$ is a second moiety, it may be linked directly to the carbon atom to which it is associated by means of a bond. On the other hand, it may be bound to such carbon through a linking group. A similar situation applies to the first reagent M1-Z wherein Z is bound to M1 through a bond or a linking group.

The first reagent may be prepared by methods that are well known to one skilled in art. Nucleophile Z may be attached directly to M1 by a bond or indirectly by a linking group. A discussion of methods of preparing a first reagent where Z is an amine group is presented below. In one embodiment Z is $NR^8R^9$ wherein $R^8$ and $R^9$ are independently selected from the group consisting of H and alkyl. Other nucleophiles include, for example, thiols, carbon nucleophiles such as malonate, acetoacetate esters, etc., and the like. For other nucleophiles methods of preparation are well known in the art. For example, see March, "Advanced Organic Chemistry," fourth addition, Appendix B: Classification of reactions by type of compound synthesized pp. 1269–1300, Wiley, Interscience, New York 1992.

The second reagent also may be prepared from readily available starting materials by methods that are well known to one skilled in art. Methods of preparation include those discussed in the references set forth in the section entitled "Description of the Related Art."

Compounds containing one or more rings mentioned above may be prepared, for example, by methods described by Patai and Rappoport, in Patai, "The Chemistry of Alkenes," vol. 1, pp. 469–584, Interscience, New York 1964.

The combination is treated under conditions sufficient to permit the formation of a product of the reaction of the first and second reagents wherein M1 becomes conjugated to the second reagent. Moderate temperatures are normally employed for carrying out the reaction and usually constant temperature, preferably, room temperature. The temperature is usually in the range from about 0° to about 80° C., more usually from about 4° to about 65° C., preferably, about 20 to about 45° C.

The amount of the first and second reagents employed in the method of the present invention is dependent on the nature of the reagents, the rate of reaction, the potential for side reactions, and so forth. Such amounts should be readily apparent to those skilled in the art. Usually, excess of one reagent over the other is used to force a reaction to completion using laws of mass action. However, stoichiometric amounts may be employed where circumstances permit. Typically, the amounts of the reagents are those necessary to achieve the result desired in accordance with the present invention. This rule is generally applicable for the above reactions as well as those discussed hereinbelow including using the compounds of the present invention to carry out an assay for an analyte.

The time period for conducting the present method is usually about 1 minute to about 12 hours, more usually about 6 to about 8 hours. The time period is dependent on the particular reactions and reagents involved. Those skilled in the art will be aware of the time requirements for a particular reaction.

In one particular embodiment of the present invention, the combination comprises a first reagent, M1'-L1'-Z', wherein M1' is a first moiety, L1' is a bond or a linking group and Z' is an amine group and a second reagent, X'—CH=CH—(C=O)(L4'M2), wherein M2' is a second moiety and L4' is a bond or a linking group. X' is selected from the group consisting of fluoro, bromo, chloro and iodo. The combination is treated under conditions sufficient to permit the formation of a product of the reaction of the first and second reagents wherein Z' displaces X' in the second reagent. M1' becomes conjugated to the second reagent to form a product of the formula: M1'-NH—CH=CH—(C=O)(L4'M2').

The first reagent possesses at least one amine group. Many molecules of interest, particularly, biological molecules, possess amine functionalities. One or more of these amine functionalities may be used in accordance with the present invention. Protecting groups may be employed to prevent one or more amine groups from interfering in the desired reaction. In some cases, it will be necessary to introduce an amine functionality into a molecule to produce the first reagent. Such methods are well known in the art and will be apparent to the skilled artisan. Examples of such procedures, by way of illustration and not limitation, include the reaction of ammonia and amines with alkyl halides, rearrangement of oximes of ketones, reduction of nitrogen-containing compounds particularly with reductive amination, the Gabriel amine synthesis, use of phthalimide, and the like. In another approach the amine-containing functionality may be attached to a molecule by a coupling reaction using a bifunctional coupling reagent such as a diamine coupling to a carboxyl-containing molecule to yield an amide with an amine functionality. A more detailed discussion of the synthesis of molecules containing an amine group may be found in March, "Advanced Organic Chemistry," fourth addition, classification of reactions by type of compound synthesized (preparation of amines), pp. 1276–1277, Wiley, Interscience, New York 1992.

Oligonucleotides containing 5'-alkylamine modifications can be synthesized using solid-phase phosphoramidite synthons. A variety of these synthons are commercially available from Glen Research. An example of such a commercially available reagent, by way of illustration not limitation, is 6-(4-monomethoxytritylamino)hexyl-(2-cyanoethyl)-(N,N-diisopropyl)-phosphoramidite. This reagent may be incorporated into an oligonucleotide sequence on the 5'-terminal end using an automated DNA synthesizer and the standard coupling cycle. After completion of the normal phosphoramidite DNA synthesis cycle, the reagent is coupled onto the 5'-hydroxyl and then oxidized to form a phosphodiester linkage. Oligonucleotides containing 3'-alkylamine modifications can be synthesized using control pore glass beads that contain a similar reagent as a linking group. The phosphoramidite DNA synthesis reagents are coupled to a hydroxyl group contained in the amino linking agent resulting in a 3'-phosphodiester linked alkyl amine. These techniques are described in more detail by Nelson, et al., Nucleic Acids Research (1992) 20(23):6253–6259. Other references for derivatizing oligonucleotides with alkyl amines are described in the following: Connolly, et al., Nucleic Acids Research (1985) 13:4485; Sproat, et al., Nucleic Acids Research (1987) 15:4837; Zuckerman, et al., Nucleic Acids Research (1987) 15:5305; Li, et al., Nucleic Acids Research (1987) 15:5275; and Dreyer, et al., Proc. Natl. Acad. Sci. USA (1985) 82:968;

The second reagent may be commercially available or may be prepared from acrylic acid, substituted acrylic acids such as halo substituted, e.g., 3-bromoacrylic acid, acrolein, propargylic acid, propargylic alcohols, and the like and derivatives thereof such as esters, amides and so forth, by methods that are well known to one skilled in art. Methods of preparation include ester formation between a substituted acrylic acid and a hydroxyl containing compound such as p-nitrophenol in the presence of dicyclohexylcarbodiimide, and so forth.

A second reagent that contains a triple bond can be prepared from the corresponding molecule containing an acetylene functionality. Representative compounds and syntheses include dehydrohalogenation of vinylic halides with strong to base, reaction of alkynes with acylating reagents, and the like.

Figure 1:
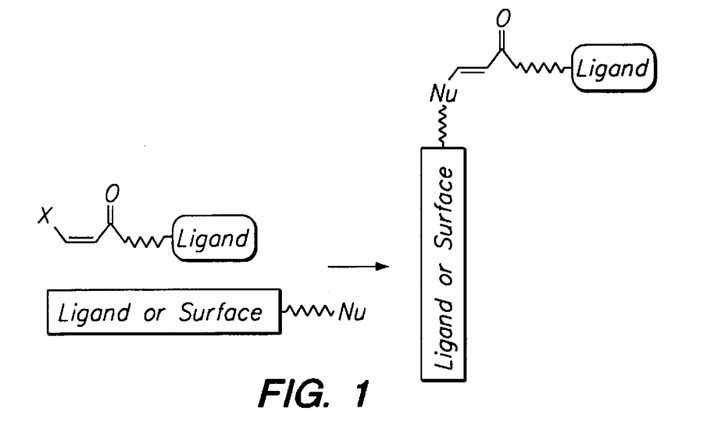
FIG. 1 is a schematic diagram depicting one embodiment of a conjugation in accordance with the present invention.

A particular embodiment of the present invention is depicted in FIG. 1 by way of illustration and not limitation. It should be noted that the figures in general might be viewed as depicting a particular stereochemistry. The figures are presented by way of example and not limitation. The present invention should not be considered to be limited to any particular stereochemistry or isomers. The first reagent has a nucleophile Nu linked to a ligand or a surface. The second reagent has a ligand linked to the carbonyl carbon, which is bound to one carbon of the carbon-carbon double bond. X is bound to the other carbon of the carbon-carbon double bond. During the reaction Nu displaces X in the second reagent. The resulting product is not capable of β-elimination rendering the product stable.

Figure 2:
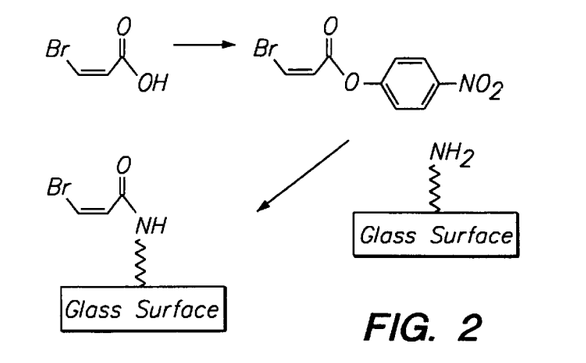
FIG. 2 is a schematic diagram depicting another embodiment of a conjugation in accordance with the present invention.
Figure 3:
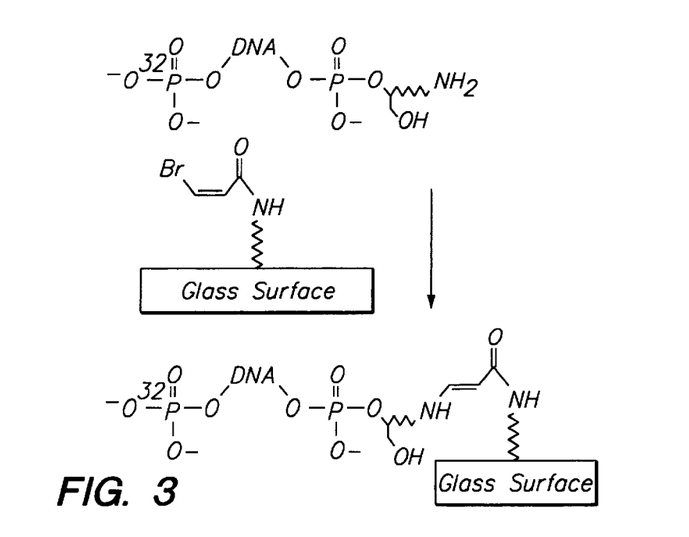
FIG. 3 is a schematic diagram depicting another embodiment of a conjugation in accordance with the present invention.

Another embodiment of the present invention is depicted in FIGS. 2 and 3. In this embodiment a second reagent is synthesized in order to incorporate a glass surface therein. The reaction utilized is known and involves, for example, formation of the p-nitrophenyl ester of bromoacrylic acid. A glass surface is derivatized by known methods such as reaction with an aminoalkyl silane derivative, e.g., trialkoxy 3-aminopropylsilane such as aminopropyltriethoxysilane (APS), 4-aminobutyltrimethoxysilane, 4-aminobutyltriethoxysilane, 2-aminoethyltriethoxysilane, and the like. APS reacts readily with oxide and/or hydroxyl groups on glass surfaces. APS provides primary amine groups that may be used to carry out the present methods. Such a derivatization procedure is described in EP 0 173 356 B1, the relevant portions of which are incorporated herein by reference. While this represents one of the preferred approaches, a variety of other attachment reactions are possible for the covalent attachment as mentioned above.

The bromoacrylic acid becomes bound to the glass surface by amide formation involving the amine functionality of the glass surface and the activated ester, namely, the p-nitrophenyl ester. A polynucleotide is employed that comprises a terminal hexylaminophosphodiester introduced by appropriate phosphoramidite chemistry. See, for example, P. Nelson, et al., Nucleic Acids Research (1989) 17:7179.

Introduction of a nucleophile such as an amine group into a nucleotide to form a modified nucleotide can be accomplished by a chemical modification of the nucleotide either as part of the nucleic acid polymer or prior to the incorporation of the modified nucleotide into the nucleic acid polymer. For example, the methods mentioned above for the synthesis of an oligonucleotide may be employed. In another approach a modified nucleotide can be produced by incorporating a modified nucleoside triphosphate into the polymer chain during an amplification reaction. For example, DNA polymerases such as Klenow fragment, RT, and Taq polymerase can be used to incorporate 5-aminoallyl-2'-deoxyuridine-5'-triphosphate during DNA synthesis. On the other hand, RNA polymerase can be used to incorporate 5-aminoallyl-uridine-5'-triphosphate during RNA synthesis.

Other ways in which a nucleophile such as an amine may be incorporated into a polynucleotide are discussed below by way of illustration and not limitation. For conjugation of ligands and reporter molecules to nucleic acids in accordance with the present invention, a two step reaction may be performed. The first step involves incorporation of modified nucleotide triphosphates that contain a primary amine group attached at the N6-position of purines or the C5-position of uridine during synthesis of DNA or RNA. The second step involves covalent attachment of a reporter molecule or ligand to the amine-labeled nucleic acid. The conjugate of a second reagent, such as bromo-acrylamide, and a ligand or a reporter molecule specifically reacts with the primary amine groups of the modified nucleosides in the DNA or RNA. DNA polymerases, such as Klenow fragment, T4, reverse transcriptase, and thermostable polymerases and T7 RNA polymerase may be used to incorporate the modified nucleotide triphosphate containing the primary amine during synthesis of DNA or RNA. For synthesis of DNA, a typical reaction would contain 1 $\mu$M DNA primer:template, 1X enzyme buffer (normally supplied by the manufacturer of the polymerase), 100 $\mu$M dATP, dCTP, and dGTP, 100 $\mu$M 5-allylamino-dUTP, and 10 units (U) DNA polymerase. The reaction mixture is incubated for 60 minutes at the appropriate temperature (75° C. for thermostable polymerases and 37° C. for all others). Under these conditions, 5-allylamino-dUTP is incorporated at every template dA position. One would predict 5-allylamino-dUTP to be an efficient substrate both in terms of incorporation and addition of the next correct dNTP that could readily substitute for the natural substrate dTTP. We have measured incorporation efficiency for other substrates that contain larger chemical moieties at the 5-position. Biotin-5-dUTP and phenylboronic acid-5-dUTP were incorporated by Klenow, MuLV RT, and Taq is DNA polymerase with relative kcat/Km values of 3–10. A relative kcat(Km of 1 indicates the compound is incorporated with similar efficiency to the natural dNTP. In addition, DNA products synthesized using these two compounds were full length indicating that they do not decrease processivity of the polymerase. By varying the ratio dTTP to 5-allylamino-dUTP, the amount of modified amine nucleotide incorporated into the newly synthesized product can be controlled.

For synthesis of amine-labeled RNA, the reaction can contain 1 $\mu$g linearized DNA template, 1X enzyme buffer (40 mM Tris-HCl, pH 8.0, 8 mM $MgCl_2$, 1 mM spermidine, 25 mM NaCl, 10 mM DTT), 10 U placental RNAse inhibitor, 500 $\mu$M CTP, GTP, ATP, 400 $\mu$M 5-allylamino-UTP, and 10 U T7 RNA polymerase. The reaction is then incubated at 37° C. for 60 min. Under these conditions, $N^6$-(6-aminohexyl)-ATP is incorporated with greater than 35% efficiency (GibcoBRL product literature), and 5—allylamino-UTP should be incorporated with similar or greater efficiency since the amine moieties are comparable in size. Also, the 5-allylamino-UTP may be incorporated with greater efficiency since the amino group is attached at the 5 position, which is not involved in hydrogen bonding. The reaction is stopped by the addition of 50 mM EDTA, and the allylamine-labeled DNA or RNA is isolated by ethanol precipitation or gel filtration on Sephadex G50. The nucleic acid then is resuspended in 10 mM Tris-HCl, pH 8.0, 1 mM EDTA.

For attachment of the reporter molecule, the sample is first heat denatured for 10 minutes at greater than about 90° C., followed by incubation on ice. The reporter molecule, e.g., bromoacrylate acrylamide-dye, is added to a final concentration of 10 mM in buffer at pH 9.0. The reaction is incubated at room temperature for 4 hours to allow covalent attachment of the reporter molecule. Unconjugated reporter molecules are then removed by centrifugation using, for example, a Microcon Centrifugal Filter Device from Amicon.

One procedure for the derivatization of the metal surface is similar to that described above for glass surfaces. One uses an aminoalkyl silane derivative, e.g., trialkoxy 3-aminopropylsilane such as aminopropyltriethoxy silane (APS), 4-aminobutyltrimethoxysilane, 4-aminobutyltriethoxysilane, 2-aminoethyltriethoxysilane, and the like. APS reacts readily with the oxide and/or hydroxyl groups on metal and silicon surfaces. APS provides primary amine groups that may be used to carry out the present methods. Such a derivatization procedure is described in EP 0 173 356 B1, the relevant portions of which are incorporated herein by reference. While this represents one of the preferred approaches, a variety of other attachment reactions are possible for both the covalent and non-covalent attachment as mentioned above.

Referring to FIG. 3, the polynucleotide comprising the amine group is combined with the bromoacrylamide reagent comprising the glass surface and the combination is incubated under conditions for displacement of the bromine group of the bromoacrylamide reagent by the amine group of the polynucleotide reagent. The product of the reaction comprises the polynucleotide attached to the glass surface. Any number of polynucleotides may be attached to the surface depending on the number of bromoacrylamide groups present. One advantage of the above reaction is that the ligand is linked to a small molecule rather than a large protein.

Substitutions of small functional groups for hydrogen in the 5'-position of uracil have only small effects on the rate of incorporation of the analog and polymerization of the next correct dNTP. For example, Klenow fragment incorporated 5'-formyl-dUTP with 71% efficiency relative to the normal substrate dTTP, and the products synthesized were comparable to those synthesized using dTTP both in terms of length and quantity.

The present invention overcomes limitations of the avidin-biotin system and the digoxigenin-antidigoxigenin system. For the avidin-biotin system, as mentioned above, such limitations include nonspecific binding attributed to the basicity of the avidin molecule, nonspecific binding attributed to the presence of carbohydrate residues on the avidin molecule, background interference associated with the presence of endogenous biotin and the large size of the avidin (about 68,000 molecular weight). In the digoxigenin-antidigoxigenin system the digoxigenin is enzymatically incorporated into the DNA and the ligand is covalently linked to Fab fragments of the antibody. Digoxigenin-dUTP is not readily incorporated by DNA polymerases and the Fab fragment attached to the ligand is about 50,000 molecular weight. The present invention provides a means for avoiding these problems.

Various ways may be employed to produce an array of polynucleotides on the surface of the glass. Such methods are known in the art. One such method is discussed in U.S. Pat. No. 5,744,305 (Fodor, et al.) and involves solid phase chemistry, photolabile protecting groups and photolithography. Binary masking techniques are employed in one embodiment of the above. In another approach ink jet technology may be used to spot polynucleotides and other reagents on a surface as described, for example, in PCT application WO 89/10977. Other methods include those disclosed by Gamble, et al., WO97/44134; Gamble, et al., WO98/10858; Baldeschwieler, et al., WO95/25116; Brown, et al., U.S. Pat. No. 5,807,522; and the like.

Figure 4:
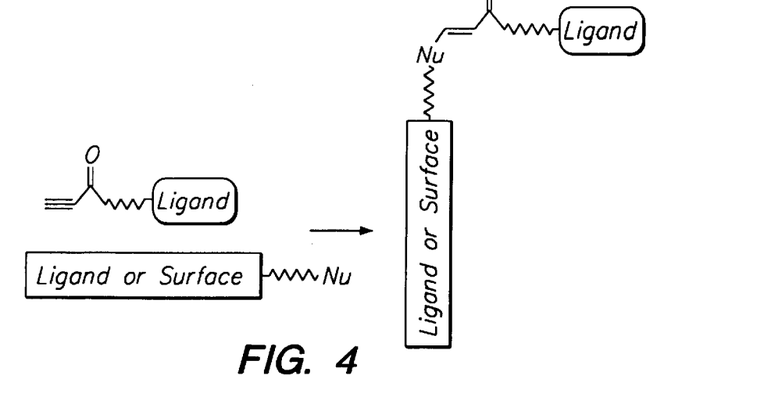
FIG. 4 is a schematic diagram depicting another embodiment of a conjugation in accordance with the present invention.

Another aspect of the present invention is depicted in FIG. 4. In this embodiment the first reagent has a nucleophile "Nu" linked to a ligand or a surface. The second reagent has a ligand linked to the carbonyl carbon thereof, which is bound to one carbon of a carbon-carbon triple bond. X is bound to the other carbon of the carbon-carbon triple bond. During the reaction nucleophile "Nu" adds to the β-carbon of the triple bond. The resulting product is highly resistant to β-elimination.

Figure 5:
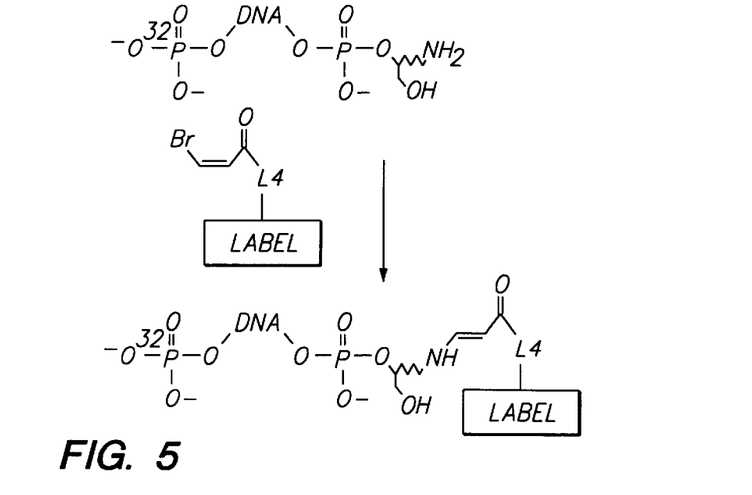
FIG. 5 is a schematic diagram depicting another embodiment of a conjugation in accordance with the present invention.

The present invention may be used to incorporate ligands, receptors and surfaces of all kinds into a molecule. For example, the present invention may be used to incorporate a label into a molecule such as a polynucleotide. One approach is shown in FIG. 5. A polynucleotide comprising an amine group is combined with the bromoacryl reagent comprising the label bound to the carbonyl carbon by L4, which may be a bond or a linking group. In one embodiment, the label has an amine functionality and is linked to the carbonyl carbon through an amide linkage. The combination is incubated under conditions for displacement of the bromine group of the bromoacrylamide reagent by the amine group of the polynucleotide reagent. The product of the reaction comprises the label attached to the polynucleotide. Any number of labels may be attached to the polynucleotide depending on the number of amine groups on the polynucleotide. Furthermore, the polynucleotide may be attached to a surface.

Figure 6:
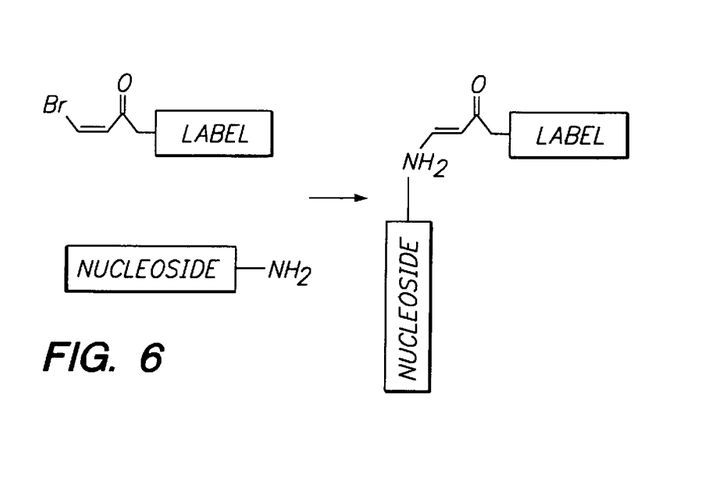
FIG. 6 is a schematic diagram depicting another embodiment of a conjugation in accordance with the present invention.

Another approach to labeling a polynucleotide is depicted in FIG. 6. A label is incorporated into a nucleoside, which then may be incorporated into a polynucleotide using known procedures such as mentioned above, e.g., for the preparation of oligonucleotides.

As can be understood, the present invention may be used to attach a label to a molecule other than a nucleoside or polynucleotide. Labels may be attached to members of a specific binding pair such as an antigen, hapten, antibody, pollutant, pesticide, drug and the like. Molecules labeled in accordance with the present invention may be adapted to many analytic techniques including by way of illustration and not limitation general chemistry techniques well known in the art, chromatographic techniques (e.g., thin layer chromatography, gas chromatography, high performance liquid chromatography, etc.), flow cytometry techniques, mass spectrometry techniques, assays such as agglutination assays, capillary precipitation assays, gel diffusion assays, specific binding pair member assays, and so forth.

Exemplary of assays involving specific binding pair members include ligand-receptor assays, e.g., antigen-antibody reactions, polynucleotide binding assays, and so forth. The assays are usually homogeneous or heterogeneous, preferably homogeneous, including competitive and sandwich. In a specific binding assay, the sample may be pretreated, if necessary, to remove unwanted materials. Where an assay utilizes a molecule that is attached to a surface, the present invention may be used, if desired, to attach the molecule to the surface. Alternatively, other procedures may be utilized and are available in the literature. See, for example, A. C. Pease, et al., Proc. Nat. Acad. Sci. USA, 91:5022–5026 (1994).

In the homogeneous assay approach the reaction usually involves one member of a specific binding pair, e.g., a specific antibody, a labeled analyte and the sample analyte. The signal arising from the label is modified, directly or indirectly, upon the binding of the specific antibody to the labeled analyte. Both the binding of the specific binding pair members and the detection of the extent thereof are carried out in a homogeneous solution. Exemplary of the homogeneous assay are assays employing enzyme labels such as the EMIT® assay described in U.S. Pat. No. 3,817,837, the disclosure of which is incorporated herein by reference, the CEDIA assay, and so forth.

In the heterogeneous approach the reagents are usually the sample, a specific binding pair member such as an antibody, and means for producing a detectable signal. The sample is generally placed on a support, such as a microtiter plate or slide, and contacted with the specific binding pair member in an aqueous phase. The support is then separated from the liquid phase and either the support phase or the liquid phase is examined for a detectable signal employing means for producing such signal, which includes a label. Exemplary of heterogeneous assays are the radioimmunoassay (RIA), immunofluorescence methods, enzyme-linked immunoassays, such as the enzyme-linked immunosorbent assay (ELISA, see U.S. Pat. Nos. 3,654,090; 3,839,153; 3850,752; 4,016,043 and Re 29,169, the disclosures of which are incorporated herein by reference).

Enzyme immunoassays (EIA's) comprise quantitative procedures in which a specific binding reaction such as, in immunological cases, the antigen-antibody reaction, is monitored by enzyme activity measurements. The term ELISA is generally used for reagent excess assays of specific antibodies or antigens. However, sometimes, it is used interchangeably with EIA and immunoenzymometric assay. There are two basic types of EIA's: heterogeneous (separation required) and homogeneous (separation free) assays. In the heterogeneous systems, since the activity of the enzyme label is not affected by the antigen-antibody reaction, it must be separated into antibody-bound and free, unbound enzyme fractions. The enzyme activity of either of these two fractions can be measured. In the homogeneous systems, the enzyme activity of the assay solution is measured without a prior physical separation of the antibody-bound enzyme to label from the free, unbound one, primarily because the activity of the bound enzyme label is significantly different from the unbound one. The various heterogeneous and homogeneous EIA's can be further characterized as either competitive or non-competitive (immunoenzymometric) assays, depending on whether the unlabeled antigen and the antigen linked to an enzyme or attached to a solid phase compete for a limited number of antibody binding sites, or whether the antigen or antibody to be measured is allowed to react alone with an excess of immune reactant. For a more detailed discussion of various enzyme assay techniques, see "Enzyme Immunoassay" by Edward T. Maggio, CRC Press, Inc., Boca Raton, Fla., 1980. See also, for example, U.S. Pat. Nos. 3,690,834; 3,791,932; 3,850,578; 3,853,987; 3,867,517; 3,901,654; 3,935,074; 3,984,533; 3,996,345 and 4,098,876, which listing is not intended to be exhaustive.

A particular assay for determining an analyte in a sample is described next. A combination is provided in a medium, usually an aqueous medium. The combination comprises a sample and at least one compound in accordance with the present invention wherein the compound forms a complex related to the presence of the analyte in the sample. In this aspect of the invention one of the first or the second moiety is capable of forming a complex with the analyte or a compound whose presence is indicative of the presence of the analyte. The complex may be formed by specific binding of the analyte and the moiety. The particular reaction conditions employed are determined by the type of assay conducted such as those mentioned above. Such reaction conditions, which include temperature, times, pH and the like are well known in the art and will not be repeated here. The compound is detected in the complex, the presence thereof indicating the presence of the analyte. The compound is represented by the formula:

$$M1-Z-C(L2'R^3)=C(L3'R^4)-Y-(L4''R^5)$$

wherein M1 is a first moiety and Z is a heteroatom, preferably nitrogen, and wherein L2', L3' and L4" are independently a bond or a linking group; and wherein one of $R^3$, $R^4$ or $R^5$ is a second moiety; and wherein Y is a carbon-carbon double bond, a carbon-heteroatom (preferably, oxygen, nitrogen or sulfur) double bond or a carbon-nitrogen triple bond wherein, when Y is a carbon-carbon double bond or a carbon-heteroatom double bond, Y may be taken together with $R^3$ or $R^4$ to form a 5 to 7 membered ring when $R^3$ or $R^4$ are not a second moiety; and wherein, when not a second moiety, $R^3$, $R^4$ and $R^5$ are independently selected from the group consisting of H, alkyl, alkenyl, alkynyl, aryl, aralkyl, heteroalkyl, heteroalkenyl, heteroalkynyl, heteroaryl, and heteroaralkyl and the like; and wherein, when $R^3$ and $R^4$ or $R^3$ and $R^5$ are not a second moiety, $R^3$ and $R^4$ or $R^3$ and $R^5$ may be taken together to form a 5 to 7 membered ring.

In a preferred embodiment relating to the determination of an analyte, one of the first or second moieties above is a label or a surface. In another preferred embodiment the compound has the formula:

$$M1'-NH-CH=CH-(C=O)(L4'M2')$$

wherein M1' is a first moiety and M2' is a second moiety and L4' is a bond or a linking group.

The present invention may be used to synthesize a polynucleotide on a surface, e.g., to prepare an array of polynucleotides on a surface. A compound of the formula:

$$X'-CH=CH-(C=O)(L4'M2'')$$

is employed wherein M2" is a surface, L4' is a bond or a linking group and X' is selected from the group consisting of fluoro, bromo, chloro and iodo. A nucleoside corresponding to the first nucleotide in the sequence of nucleotides forming the polynucleotide is modified by incorporation of an amine functionality by methods referred to above. The modified nucleotide is combined with the above compound under conditions for nucleophilic displacement of X and attachment of the nucleoside to the compound by means of the amine group.

The attached nucleotide may be used to construct the polynucleotide by means well known in the art. For example, in the synthesis of arrays of oligonucleotides, nucleoside monomers are generally employed. In this embodiment an array of the above compounds is attached to the surface and each compound is reacted to attach a nucleoside. The array of compounds may be formed on the surface utilizing one of the methods mentioned above for forming arrays such as ink-jet spotting, masking technology, and so forth. Nucleoside monomers are used to form the polynucleotides usually by phosphate coupling, either direct phosphate coupling or coupling using a phosphate precursor such as a phosphite coupling. Such coupling thus includes the use of amidite (phosphoramidite), phosphodiester, phosphotriester, H-phosphonate, phosphite halide, and the like coupling. One preferred coupling method is the phosphoramidite coupling, which is a phosphite coupling. In using this coupling method, after the phosphite coupling is complete, the resulting phosphite is oxidized to a phosphate. Oxidation can be effected with oxygen to give phosphates or with sulfur to give phosphorothioates. The phosphoramidites are dissolved in anhydrous acetonitrile to give a solution having a given ratio of amidite concentrations. The mixture of known chemically compatible monomers is reacted to a solid support, or further along, may be reacted to a growing chain of monomer units. For a more detailed discussion of the chemistry involved in the above synthetic approaches, see, for example, U.S. Pat. No. 5,436,327 at column 2, line 34, to column 4, line 36, which is incorporated herein by reference in its entirety.

In another approach an oligonucleotide that comprises an amine functionality at or near the 5' or 3' end portion, which is reactive with the carbon attached to X', is employed. In one embodiment the amine functionality is part of a nucleotide in the oligonucleotide, preferably, at or near the end portion of the oligonucleotide that is to become attached to the reagent. As a result the oligonucleotide becomes attached to the surface. Arrays of oligonucleotides may be prepared in this manner.

Amine functionalities may be incorporated into cDNA by utilizing amine-modified nucleoside triphosphates or amine-substituted primers during PCR amplification in bacterial plasmids. The amine-containing cDNA is then reacted with the second reagent of the present invention as described above.

In still another approach cDNA may be attached to a surface utilizing the above second reagent of the invention. The above surface may be contacted with a solution containing cDNA usually by spotting the cDNA solution onto the surface that has the second reagent attached thereto. The material is then subjected to conditions for cross-linking using ultraviolet light.

The oligonucleotide arrays may be used to carry out nucleic acid hybridization in a diagnostic fashion. To this end the array is exposed to a solution containing polynucleotide analytes in the usual manner and labeled DNA fragments selectively hybridize at sites where a complementary oligonucleotide is found. Other approaches utilizing the oligonucleotide arrays produced in accordance with the present invention will be apparent to those skilled in the art.

One or more of the above reagents may be provided as a kit in packaged combination with one another or with reagents for conducting an assay. To enhance the versatility of the subject invention, the reagents can be provided in the same or separate containers so that the ratio of the reagents provides for substantial optimization of the method or assay. The reagents may each be in separate containers or various reagents can be combined in one or more containers depending on the cross-reactivity and stability of the reagents.

The kit can further include other separately packaged reagents for conducting an assay such as enzyme substrates, additional sbp members, ancillary reagents and so forth. The relative amounts of the various reagents in the kits can be varied widely to provide for concentrations of the reagents that substantially optimize the reactions that need to occur during the present method and to further substantially optimize the sensitivity of the assay. The kit can further include a written description of a method in accordance with the present invention as described above.

EXAMPLES

The invention is demonstrated further by the following illustrative examples. Parts and percentages recited herein

Example 1

Preparation of p-nitrophenyl-3-bromoacrylate

In a 500 ml dry round bottom flask, 7.55 g (0.05 mole) of 3-bromoacrylic acid (from Omega Chemical Company, Montreal, Canada) was dissolved in 100 ml of anhydrous 1,4-dioxane. To this solution was added successively with stirring 7.7 g (0.055 moles) of p-nitrophenol (from Aldrich Chemical Company, Milwaukee, Wis.) and 11.4 g (0.055 moles) of dicyclohexylcarbodiimide (DCC) from Aldrich Chemical Company). The reaction was allowed to proceed overnight at room temperature protected from light. The reaction mixture was filtered and the precipitate was washed 2 or 3 times with fresh anhydrous 1,4-dioxane. The filtrate and the wash solutions were combined and concentrated under vacuum. The oily residue was subjected to silica gel chromatography using methylene chloride as the eluent. The fractions containing product were combined and concentrated under vacuum to give a white solid.

Example 2

Preparation of Glass Slides with Reactive Amine Surface

Clean glass microscope slides (25) were washed and placed in a Teflon® slide holder. Anhydrous toluene (800 ml) was placed in a 2-liter reaction vessel into which the slide holder had been placed. The toluene was stirred vigorously. To the stirring toluene was added 34.4 g (0.156 moles) of 3-aminopropyltriethoxysilane (Aldrich Chemical Company). The reaction was allowed to proceed with stirring for one hour at room temperature. The glass slides were removed from the reaction vessel and were rinsed with anhydrous toluene. The slides were then rinsed successively with acetone and 2-propanol and then were dried with a stream of nitrogen. The dry slides were placed in a vacuum oven and dried at 150° C. at 1 mm Hg for one hour.

Example 3

Preparation of Glass Slides with High Density, Hydrophilic, Reactive Amine Surface Clean glass microscope slides (25) were washed and placed in a Teflon® slide holder. The holder containing the slides was placed into a 2-liter reaction vessel and purged with $N_2$ for 1 hr. In a 1000 ml oven-dried bottle capped with a septum, 800 ml of anhydrous toluene was cannulated and 10 g of 11-Bromoundecyl trichlorosilane (from Gelest Inc., Tullytown, Pa.) was added via a syringe. The silane solution was swirled to dissolve the contents and transferred to the reactor via a cannula. The silylation was carried out at room temperature for 2 hours under $N_2$ atmosphere. The silane solution was then removed from the reactor and replaced with 800 ml of fresh anhydrous toluene. After 5 minutes of stirring, the boat containing the silylated slides was removed from the reactor and put into a fresh toluene wash. The holder was washed thoroughly in the toluene. The toluene was removed and the slides were then washed with 800 ml of acetonitrile. The slides were dried with a stream of $N_2$ and stored in a dry box prior to final conversion with 4,7,10-Trioxa-1,13-tridecanediamine (from Aldrich Chemical Company). The silylated slides obtained as described above were placed into a 2-liter reactor. The reactor was filled with 800 ml of 4,7,10-Trioxa-1,13-tridecanediamine and warmed to 100° C. The reaction was maintained at 100° C. overnight. The next morning the reaction was cooled to room temperature, the slides were removed from the reactor and were washed in a beaker successively with dimethylformamide (twice), acetonitrile (twice), by dipping the boat continuously up and down in the solvent wash. The slides were dried with a stream of $N_2$, wrapped in aluminum foil and stored in a dry box.

Example 4

Preparation of Glass Slides with Reactive Bromoacrylate Surface p-Nitrophenyl-3-bromoacrylate (10.88 g) prepared as in Example 1 was combined with stirring with 800 ml of anhydrous dichloromethane (from Aldrich Chemical Company) in a 1 liter round bottom flask to produce a 0.05 M solution. This solution was added to a reaction vessel (Teflon® boat) containing the slides prepared as in Example 3. The reaction solution was stirred overnight at room temperature under a nitrogen purge. The reaction solution was removed from the reactor. The Teflon boat was removed from the reactor and the slides were washed by immersion in a beaker. The slides were first washed twice with 700 ml of dichloromethane and then twice with 700 ml of acetonitrile (from Aldrich Chemical Company) followed by washing with methanol and finally with distilled water. The slides were dried under nitrogen and stored in an inert atmosphere.

Example 5

Attachment of Synthetic Oligonucleotides containing Either 3', or 5' alkyl Amine Moieties to a Surface The 5'- or 3'-amine-terminated oligonucleotides were dissolved in 0.05 M sodium carbonate buffer (pH 9.0) containing 0.005% Triton x-100 at a concentration of 10 µM. The oligonucleotides were spotted onto the surface via pipette, pin or inkjet. The spots were allowed to dry and then were inspected visually for the appearance of salt crystals. The surfaces were placed into a humid chamber and the spots were allowed to re-hydrate. The attachment reaction was allowed to proceed for 12 hours; then, the surfaces were removed from the chamber and the spots were allowed to dry once again. The excess DNA was removed from the surface and the unreacted functional groups were passivated by treatment with a glycine solution. The surfaces were placed in a Teflon® slide holder, and the holder was placed in a beaker containing 0.5 M sodium glycinate, pH 11.0 (+0 0.005% Triton X-100) for 20 minutes under stirring. The surfaces were washed with copious amounts of deionized water over a period of 5 min. This wash step was repeated 2 times. The surfaces were dried by centrifugation.

Example 6

Attachment of PCR Amplified Products Containing a 5'-alkyl Amine Antisense Strand from cDNA Inserts on Bacterial Plasmids Preparation of cDNA The following reagents were employed: 10 mM Tris pH 8.3 (Tris(hydroxymethyl)aminomethane-HCl from Sigma Chemical Company, St. Louis, Mo.), 3.5 mM $MgCl_2$, 25 mM KCl, 0.2 mM each dNTP, 0.4 µM each primer, 2 ng template per 100 µl reaction mixture and 12.5 units TaqGold® polymerase (from PE BioSystems, Foster City Calif.) per 100 µl reaction mixture.

The plasmid, vector (designated PT7T3) and cDNA for PCR replication were obtained from Jeffery Trent of the National Institutes of Health, Institute for Genomic Research (Bethesda, Md.). The primers were based on the M13 sequences of the plasmid. The primers were produced on an ABI 394 DNA synthesizer using standard phosphoramidite monomers. The primer that would produce the antisense strand in the amplified product was synthesized with a 5'-Alkyl Amine as described previously.

PCR was carried out according to standard procedures. After PCR one-tenth of the total reaction volume of 3 M sodium acetate (pH 6.0) and one volume equal to the reaction volume of isopropanol was added to the reaction mixture, which was frozen and spun for 10 min at 14 rpm. The supernatant was removed and the pellet was with 1 ml of 70% ethanol. The supernatant was removed completely and the pellet was dried briefly (approximately 2 minutes). The pellet was resuspended in water or sodium chloride-sodium citrate (SSC) buffer, pH 8.0, and the suspension was incubated at 65° C. for 2 hr to resuspend the pellet. The mixture was subjected to microfugation for 10 min using a Microcon centrifugal device and the supernatant was removed from the pellet.

Spotting of cDNA

The cDNA from above in 1× or 3×SSC at 0.25 to 0.5 mg/ml (estimated from agarose gel quantitation). The cDNA solutions were spotted onto the slides prepared as in Example 3 using an inkjet spotter. The spots were allowed to dry and they were inspected visually for the appearance of salt crystals. The slides were placed into a humid chamber and the spots are allowed to re-hydrate. The attachment reaction was allowed to proceed for 12 hours then the slides were removed from the chamber and the spots allowed to dry once again. The excess DNA was removed from the surface and the unreacted functional groups were passivated by treatment with a glycine solution The slides were soaked in a 0.5 M sodium glycinate solution (pH 11.0) for 20 min. The surface attached double stranded PCR products were denatured by soaking the slides in 50 mM sodium hydroxide for 2 min at room temperature. The slides were washed with deionized water, rinsed briefly in 100% ethanol and dried by centrifugation.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound useful as a component of a specific binding assay, said compound having the formula:

$$M1'\text{-}NH\text{---}CH\text{=}CH\text{---}(C\text{=}O)(L4'M2')$$

wherein M1' is a small molecule ligand, a large molecule ligand or a surface and M2' is a small molecule ligand, a large molecule ligand or a surface wherein one of said M1' or said M2' is a large molecule ligand or a surface and L4' is a bond or a linking group.

2. A compound of the formula:

$$M1'\text{-}NH\text{---}CH\text{=}CH\text{---}(C\text{=}O)(L4'M2')$$

wherein M1' is a biomolecule or a surface and M2' is a surface and L4' is a bond or a linking group.

3. A compound of the formula:

$$M1'\text{-}NH\text{---}CH\text{=}CH\text{---}(C\text{=}O)(L4'M2')$$

wherein M1' is a polynucleotide and M2' is a surface and L4' is a bond or a linking group.

4. A compound according to claim 3 wherein said polynucleotide is an oligonucleotide.

5. A compound according to claim 3 wherein said polynucleotide is DNA, RNA, m-RNA, r-RNA, t-RNA, cDNA, or a DNA-RNA duplex.

6. A compound useful as a component of a specific binding assay, said compound comprising an array of M1'-NH—CH=CH—(C=O)(L4')- that is linked to M2' wherein M1' is a polynucleotide and M2' is a surface and (L4')- is a bond or a linking group.

7. A compound according to claim 1 wherein said M2' small molecule ligand or a large molecule ligand selected from the group consisting of proteins, peptides, polysaccharides, hormones, nucleic acids, labels, antigens and haptens.

* * * * *